United States Patent
Komure et al.

(10) Patent No.: US 10,772,814 B2
(45) Date of Patent: Sep. 15, 2020

(54) HOT RESHAPING PROCESS

(71) Applicant: L'OREAL, Paris (FR)

(72) Inventors: Natsumi Komure, Kawasaki (JP); Laetitia Feuillette, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/572,287

(22) PCT Filed: May 12, 2016

(86) PCT No.: PCT/JP2016/064806
§ 371 (c)(1),
(2) Date: Nov. 7, 2017

(87) PCT Pub. No.: WO2016/182086
PCT Pub. Date: Nov. 17, 2016

(65) Prior Publication Data
US 2018/0098928 A1  Apr. 12, 2018

(30) Foreign Application Priority Data

May 12, 2015  (JP) ................................. 2015-097251

(51) Int. Cl.
| | | |
|---|---|---|
| *A61K 8/44* | (2006.01) | |
| *A61K 8/46* | (2006.01) | |
| *A61Q 5/04* | (2006.01) | |

(52) U.S. Cl.
CPC .............. *A61K 8/44* (2013.01); *A61K 8/466* (2013.01); *A61Q 5/04* (2013.01); *A61K 2800/30* (2013.01); *A61K 2800/805* (2013.01)

(58) Field of Classification Search
CPC .... A61K 8/44; A61K 8/466; A61K 2800/805; A61K 2800/30; A61Q 5/04
See application file for complete search history.

(56) References Cited

U.S. PATENT DOCUMENTS

| | | | | |
|---|---|---|---|---|
| 3,823,232 A | * | 7/1974 | Galerne et al. ........... | A61K 8/44 424/70.4 |
| 4,459,284 A | | 7/1984 | Azuma et al. | |
| 2012/0148517 A1 | | 6/2012 | Gilmore et al. | |

FOREIGN PATENT DOCUMENTS

| | | |
|---|---|---|
| CN | 101495087 A | 7/2009 |
| CN | 103945826 A | 7/2014 |
| CN | 105120833 A | 12/2015 |
| EP | 0 129 807 A2 | 1/1985 |
| JP | 62-9566 B2 | 2/1987 |
| WO | 2011/074136 A1 | 6/2011 |
| WO | 2011/155076 A1 | 12/2011 |
| WO | 2016/102543 A1 | 6/2016 |

OTHER PUBLICATIONS

Author: unknown, Title: Get to Know FAT CURLS, posted Jun. 25, 2013, text downloaded from https://www.naturallycurly.com/curlreading/kinky-hair-typea/get-to-know-fat-curls.*
Kothandam et al, title: TAURINE, "A Key Amino Acid in the Drug Discovery"—A Review, Asian Journal of Biomedical & pharmaceutical sciences, vol. 2, No. 12, pp. 21-27, 2012. (Year: 2012).*
International Search Report for PCT/JP2016/064806 dated Jul. 27, 2016.
Chinese Office Action for counterpart Application No. 201680026959. X, dated Nov. 5, 2019, partial translation (Search Report Only).

* cited by examiner

*Primary Examiner* — Yanzhi Zhang
(74) *Attorney, Agent, or Firm* — The Marbury Law Group, PLLC

(57) ABSTRACT

The present invention relates to a composition for reshaping keratin fibers, preferably the hair, having a specific range of a pH and including at least one specific active compound in an amount of 8% by weight or more relative to the total weight of the composition. The composition according to the present invention is preferably a cosmetic composition, for keratin fibers, such as hair, and can be used for a process for reshaping the keratin fibers with heat. The process according to the present invention can be used to deform or reshape keratin fibers, preferably hair, and can provide the keratin fibers with sufficient reshaping efficiency such as strong wave intensity of the curled keratin fibers and excellent hair conditioning effects (less damage to the keratin fibers), in a relatively short period of time as compared to a conventional process which uses a reducing agent and an oxidizing agent.

10 Claims, No Drawings

HOT RESHAPING PROCESS

CROSS REFERENCE TO RELATED APPLICATIONS

This is a national stage application of PCT/JP2016/064806, filed internationally on May 12, 2016, which claims priority to Japanese Application No. 2015-097251, filed on May 12, 2015, both of which are incorporated by reference herein in their entireties.

TECHNICAL FIELD

The present invention relates to a process, in particular a cosmetic process, for keratin fibers such as hair.

BACKGROUND ART

In long-lasting deformation of keratin fibers such as hair, first the disulphide bonds —S—S— of the keratin (cystine) are opened using a composition containing a suitable reducing agent (reduction stage), then the hair thus treated is optionally rinsed, secondly the disulphide bonds are reconstituted by applying, on the keratin fibers previously put under tension (curlers etc.), an oxidizing composition (oxidation stage, also called fixation) so as to finally give the keratin fibers the desired form. This technique thus makes it possible to carry out either waving or straightening of the keratin fibers. For example, JP-B-S62-9566 or U.S. Pat. No. 4,459,284 discloses a standard process for permanent waving or straightening of keratin fibers such as hair in line with the above steps.

The new shape imposed on the keratin fibers by chemical treatment as described above is relatively long-lasting and notably withstands the action of washing with water or shampoo, in contrast to the simple conventional techniques of temporary styling by using foams, styling gels, or lacquers.

Many compositions and processes for the above chemical treatment have been proposed. Generally, they offer good performance on the day of treatment.

However, there are various drawbacks such as follows in the above chemical treatment process that may not be suitable from the view-point of consumer's or hair-dresser's expectations:

Insufficient reshaping efficiency such as weak wave intensity;
Poor usability caused by, for example, dripping of the composition from the hair;
High levels of keratin fiber degradation, especially in repeated applications or in combination with other chemical treatments such as oxidative coloration;
Long processing time; and
Malodor of ammonia or sulfur-containing compounds during and after the deformation process.

In particular, sufficient reshaping efficiency, short processing time, and conditioning effects to keratin fibers are important. There is indeed a need to improve a deformation process of keratin fibers to provide sufficient reshaping efficiency, such as strong wave intensity of the curled keratin fibers, as well as excellent hair conditioning effects such as conditioning feel, in a relatively short period of time. In addition, excellent usability such as no or reduced malodor is also desirable.

DISCLOSURE OF INVENTION

An objective of the present invention is to provide a composition, preferably a cosmetic composition, for keratin fibers, such as hair, which can be used for a process for reshaping the keratin fibers with heat, and can provide the keratin fibers with sufficient reshaping efficiency such as strong wave intensity of the curled keratin fibers and excellent hair conditioning effects (providing hair smooth and soft feel), in a relatively short period of time, with, if possible, no malodor or reduced malodor.

The above objective of the present invention can be achieved by a composition, in particular a cosmetic composition, for keratin fibers, preferably the hair, comprising:
(a) at least one compound chosen from alkylaminosulfonic acids and those of the following formula (I) and (II):

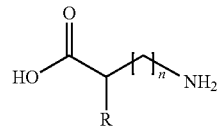

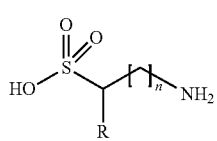

in which formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium, and
n is 0 or 1,
in an amount of 8% by weight or more relative to the total weight of the composition,
wherein
the composition has a pH of from 8 to 12, preferably from 8.5 to 11.5, and more preferably from 9.0 to 11.0.

It is preferable that the pH of the composition according to the present invention be within ±2 relative to the pH which is equal to the pKa of the following equilibrium:

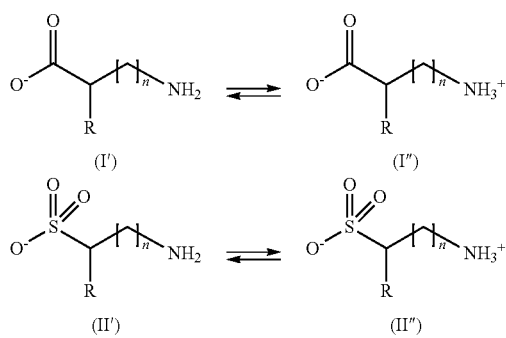

The (a) compound may be selected from the group consisting of: alkylaminosulfonic acids such as 2-(cyclohexylamino)ethanesulfonic acid; amino acids such as glycine, alanine, glutamic acid, aspartic acid, phenyl alanine, β-alanine, isoleucine, leucine, glutamine, serine, threonine, valine, tryptophane, and tyrosine; oligomers of amino acids such as glycylglycine; aminosulfonic acids such as taurine; and mixtures thereof.

It is preferable that the (a) compound be selected from the group consisting of 2-(cyclohexylamino)ethanesulfonic acid, glycine, alanine, taurine, and mixtures thereof.

The (a) compound may be the only active ingredient for reshaping keratin fibers.

The amount of the (a) compound in the composition according to the present invention may be from 8 to 25% by weight, preferably from 8.5 to 20% by weight, and more preferably from 9 to 15% by weight, relative to the total weight of the composition.

It is preferable that the composition according to the present invention comprise (b) at least one alkaline agent, and preferably an inorganic alkaline agent.

The (b) alkaline agent may be selected from the group consisting of alkaline metal hydroxides; and alkaline earth metal hydroxides, alkaline metal phosphates and or monohydrogenophosphates.

The amount of the (b) alkaline agent in the composition according to the present invention may be from 0.1 to 15% by weight, preferably from 0.2 to 10% by weight, more preferably from 0.3 to 8% by weight, and even more preferably from 0.4 to 5% by weight, relative to the total weight of the composition.

It is preferable that the composition according to the present invention does not comprise any ammonia or a thiol compound, or comprise less than 1%, preferably less than 0.5%, and more preferably less than 0.1% by weight of ammonia or a thiol compound, relative to the total weight of the composition.

It is preferable that the composition according to the present invention does not comprise any reducing agent or oxidizing agent, or comprise less than 1%, preferably less than 0.5%, and more preferably less than 0.1% by weight of a reducing agent or an oxidizing agent, relative to the total weight of the composition.

The present invention also relates to a reshaping process, in particular permanent waving, for keratin fibers, preferably the hair, comprising the steps of:
applying onto the keratin fibers the composition according to the present invention; heating the keratin fibers; and optionally rinsing and/or drying the keratin fibers.

It is preferable that the keratin fibers be heated at a temperature of at least 80° C.

The process according to the present invention can be used to deform or reshape keratin fibers, preferably hair, and can provide the keratin fibers with sufficient reshaping efficiency such as strong wave intensity of the curled keratin fibers and excellent hair conditioning effects (soft feel and smooth feel), in a relatively short period of time as compared to a conventional process which uses a reducing agent and an oxidizing agent, with, if possible, no malodor or reduced malodor.

BEST MODE FOR CARRYING OUT THE INVENTION

After diligent research, the inventors have found that the use of a specific composition under specific conditions in a process for reshaping keratin fibers, in particular hair can provide the keratin fibers with sufficient reshaping efficiency such as strong wave intensity of the curled keratin fibers and excellent hair conditioning effects, in a relatively short period of time, with, if possible, no malodor or reduced malodor.

Thus, the composition, preferably a cosmetic composition for reshaping, in particular permanent waving, keratin fibers, preferably the hair, comprises:
(a) at least one compound chosen from alkylaminosulfonic acids and those of the following formula (I) and (II):

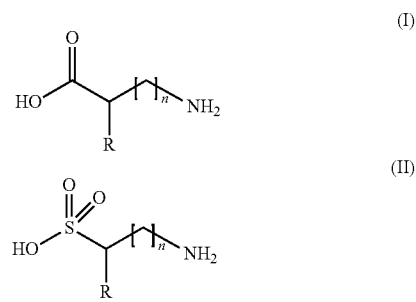

in which formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)$_2$—OH, —C(O)—O$^-$M$^+$, —S(O)$_2$—O$^-$M$^+$, and mixtures thereof with M$^+$ representing a cationic counterion such as an alkali metal, alkaline-earth metal, or ammonium, and
n is 0 or 1, in an amount of 8% by weight or more relative to the total weight of the composition,
wherein
the composition has a pH of from 8 to 12, preferably from 8.5 to 11.5, and more preferably from 9.0 to 11.0.

Hereafter, each of the composition according to the present invention and the process according to the present invention will be described in a detailed manner.
[Composition]

The composition for reshaping keratin fibers with heat according to the present invention comprises (a) at least one compound chosen from alkylaminosulfonic acids and those of the following formula (I) and (II):

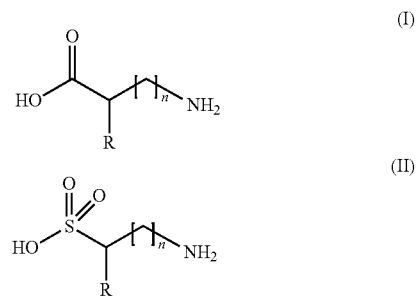

in which formulae (I) and (II)
R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)₂—OH, —C(O)—O⁻M⁺, —S(O)₂—O⁻M⁺, and mixtures thereof with M⁺ representing a cationic counterion such as an alkali metal, alkaline-earth metal, or ammonium, and n is 0 or 1, in an amount of 8% by weight or more relative to the total weight of the composition, wherein the composition has a pH of from 8 to 12, preferably from 8.5 to 11.5, and more preferably from 9.0 to 11.0.

It is preferable that the above composition be a cosmetic composition, in particular for reshaping keratin fibers. It is preferable that the keratin fibers be hair.

(Active Compound)

The composition according to the present invention comprises (a) at least one compound chosen from alkylaminosulfonic acids and those of the above formula (I) and (II), as active ingredient(s) for the hot reshaping process for keratin fibers. Two or more of the (a) compounds may be used in combination. Thus, a single type of the (a) compound or a combination of different types of the (a) compounds may be used.

The (a) compound(s) may be the only active ingredient(s) for reshaping keratin fibers in the composition according to the present invention.

The alkylaminosulfonic acid may preferably have a $C_1$-$C_{20}$ alkyl group, preferably $C_5$-$C_{16}$ cycloalkyl group, and more preferably a $C_6$-$C_{12}$ cycloalkyl group, bonded to an imino group (—NH—) and a sulfonic acid moiety. The alkylaminosulfonic acid may be selected from the group consisting of 4-(2-hydroxyethyl)-1-piperazineethanesulfonic acid, 2-(cyclohexylamino)ethanesulfonic acid, and mixtures thereof.

The (a) compound(s) of the above formula (I) and (II) may be in their non-ionized form (I) or (II) or in their ionized or betaine form (I') or (II'):

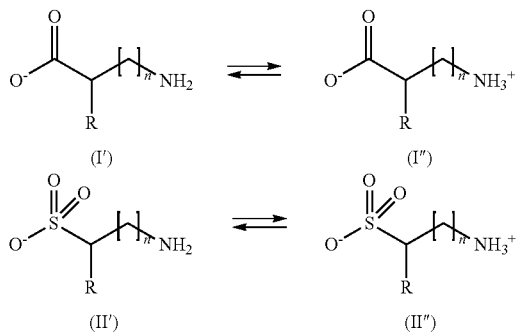

wherein

R represents a hydrogen atom, or a linear or branched, preferably linear, $C_1$-$C_5$ alkyl group, said alkyl group being optionally substituted with at least one group chosen from a hydroxyl group, an amino group, a carboxamido group, a $C_6$-$C_{18}$ aromatic group, a heterocyclic group, —C(O)—OH, —S(O)₂—OH, —C(O)—O⁻M⁺, —S(O)₂—O⁻M⁺, and mixtures thereof with M⁺ representing a cationic counterion such as an alkali metal, alkaline-earth metal, or ammonium, and n is 0 or 1, in an amount of 8% by weight or more relative to the total weight of the composition, and the composition has a pH of from 8 to 12, preferably from 8.5 to 11.5, and more preferably from 9.0 to 11.0.

As the $C_1$-$C_5$ alkyl group, mention may be made of a methyl group, an ethyl group, a propyl group, an isopropyl group, an n-butyl group, a sec-butyl group, an iso-butyl group, a tert-butyl group and a pentyl group. A methyl group and an ethyl group are preferable, and a methyl group is more preferable.

As the amino group, mention may be made of —NH₂, a group including —NH₂ such as a sulfonylamino group, and a group including —NH—R' (wherein R' denotes a hydroxyl group or a $C_1$-$C_5$ alkyl group as mentioned above) such as a hydroxyamino group and a $C_1$-$C_5$ alkylamino group. It should be noted that the term "amino" group here does not mean a part of a urea group. As the amino group, —NH₂ is preferable.

As the $C_6$-$C_{18}$ aromatic group, mention may be made of a monovalent $C_6$-$C_{18}$ aryl group such as a phenyl group and a substituted phenyl group such as a hydroxyphenyl group and an aminophenyl group, and a monovalent $C_7$-$C_{18}$ aralkyl group such as a tolyl group.

As the heterocyclic group, mention may be made of a monovalent, saturated or unsaturated, substituted or unsubstituted heterocyclic group, such as a substituted or unsubstituted pyrrolyl group, a substituted or unsubstituted pyrrolidinyl group, a substituted or unsubstituted pyridyl group, a substituted or unsubstituted piperidono group, a substituted or unsubstituted piperidinyl group, a substituted or unsubstituted morpholino group, a substituted or unsubstituted morpholinyl group, a substituted or unsubstituted furyl group, and a substituted or unsubstituted indolyl group such as 3-indolyl group.

The (a) compounds of the above formula (I) and (II) correspond to amino acids and aminosulfonic acids, respectively.

The (a) compound(s) is(are) preferably chosen from "neutral" or "acidic" amino acids or aminosulfonic acids. The term "neutral" is intended to mean amino acids or aminosulfonic acids which have a pH, at ambient temperature (25° C.), in water of inclusively between 5 and 7. The term "acidic" is intended to mean amino or aminosulfonic acids which have a pH, at ambient temperature, in water of less than 6.

Preferably, the amino acids or aminosulfonic acids may comprise a number of amino groups less than or equal to the number of acid groups.

The (a) compound(s) may be selected from the group consisting of alkylaminosulfonic acids such as 2-(cyclohexylamino)ethanesulfonic acid; amino acids such as glycine, alanine, glutamic acid, aspartic acid, phenylalanine, β-alanine, isoleucine, leucine, glutamine, serine, threonine, valine, tryptophan, and tyrosine; oligomers of amino acids such as glycylglycine; aminosulfonic acids such as taurine; and mixtures thereof.

It is preferable that the (a) compound be selected from the group consisting of 2-(cyclohexylamino)ethanesulfonic acid, glycine, alanine, taurine, and mixtures thereof.

The amount of the (a) compound(s) in the composition according to the present invention may be from 8 to 25% by weight, preferably from 8.5 to 20% by weight, and more preferably from 9 to 15% by weight, relative to the total weight of the composition.

In some cases, the amount of the (a) compound(s) in the composition according to the present invention may be from more than 10 to 30% by weight, preferably from 12 to 25% by weight, and more preferably from 15 to 20% by weight, relative to the total weight of the composition.

(Alkaline Agent)

The composition according to the present invention may comprise (b) at least one alkaline agent. Two or more (b) alkaline agents may be used in combination. Thus, a single type of alkaline agent or a combination of different types of alkaline agents may be used.

The (b) alkaline agent is different from the (a) compound.

It is preferable that the composition according to the present invention include (b) alkaline agent(s), if the (a) compound can function to reduce the pH of the composition.

The (b) alkaline agent may be an inorganic alkaline agent. It is preferable that the (b) alkaline agent be non-volatile. It is preferable that the inorganic alkaline agent be selected from the group consisting of alkaline metal hydroxides; alkaline earth metal hydroxides; alkaline metal phosphates and monohydrogen phosphates such as sodium phosphate or sodium monohydrogen phosphate.

As examples of the inorganic alkaline metal hydroxides, mention may be made of sodium hydroxide, lithium hydroxide and potassium hydroxide. As examples of the alkaline earth metal hydroxides, mention may be made of calcium hydroxide and magnesium hydroxide. As the inorganic alkaline agent, sodium hydroxide and potassium hydroxide are preferable.

The (b) alkaline agent may be an organic alkaline agent. It is preferable that the organic alkaline agent be selected from the group consisting of basic amino acids, monoamines and diamines.

The basic amino acid comprises an additional amine function optionally included in a ring or in a ureido function. Such basic amino acids may be preferably chosen from those corresponding to formula (A) below:

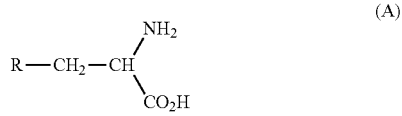

(A)

in which R denotes a group chosen from:

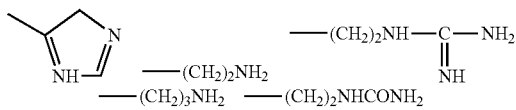

The compounds corresponding to formula (A) may be histidine, lysine, arginine, ornithine and citrulline As examples of the monoamines, mention may be made of alkanolamines such as mono-, di- and tri-ethanolamines, comprising 1 to 3 hydroxyalkyl($C_1$-$C_4$) groups. Particularly, alkanolamines may be selected from monoethanolamine, diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino) methane.

The diamines may be described in the structure (B) below:

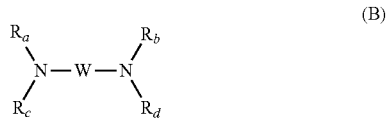

(B)

wherein W denotes an alkylene such as propylene optionally substituted by a hydroxyl or a $C_1$-$C_4$ alkyl radical, and $R_a$, $R_b$, $R_c$ and $R_d$ independently denote a hydrogen atom, an alkyl radical or a $C_1$-$C_4$ hydroxyalkyl radical, which may be exemplified by 1,3-propanediamine and derivatives thereof.

The (b) alkaline agent(s) may be used in a total amount of from 0.1 to 15% by weight, preferably from 0.2 to 10% by weight, more preferably from 0.3 to 8% by weight, and even more preferably from 0.4 to 5% by weight, relative to the total weight of the composition, depending on their solubility.

(Acid)

The composition according to the present invention may comprise at least one acid which is different from the (a) compound. Two or more acids may be used in combination. Thus, a single type of acid or a combination of different types of acids may be used.

The acid may be used to adjust the pH of the composition according to the present invention.

It is preferable that the composition according to the present invention include acid(s), if the (a) compound can function to increase the pH of the composition.

As the acid, mention may be made of any inorganic or organic acids which are commonly used in cosmetic products such as citric acid, lactic acid, sulfuric acid, phosphoric acid or hydrochloric acid (HCl). HCl is preferable.

The acid(s) may be used in a total amount of from 0.1 to 15% by weight, preferably from 0.2 to 10% by weight, more preferably from 0.3 to 5% by weight, relative to the total weight of the composition, depending on their solubility.

(Other Ingredients)

The composition of the invention may be aqueous or anhydrous. It is preferably aqueous and then comprises water at a concentration ranging from 10% to 99%, better still from 30% to 99% and even better still from 50% to 98% by weight relative to the total weight of the composition.

The composition may in particular comprise one or more organic solvents that are in particular water-soluble, such as $C_1$-$C_7$ alcohols; mention may in particular be made of $C_1$-$C_7$ aliphatic monoalcohols, for instance ethanol, or $C_6$-$C_7$ aromatic monoalcohols, which may be used alone or as a mixture with water.

The composition used in the process of the invention may also comprise at least one customary cosmetic ingredient, chosen in particular from; oils; solid fatty substances and in particular $C_8$-$C_{40}$ esters, $C_8$-$C_{40}$ acids; $C_8$-$C_{40}$ alcohols, sunscreens; moisturizers; antidandruff agents; antioxidants; chelating agents; nacreous agents and opacifiers; plasticizers or coalescers; fillers; emulsifiers; polymers, in particular conditioning polymers, such as cationic polymers; fragrances; silanes; crosslinking agents; surfactants including anionic, cationic, amphoteric and nonionic surfactants. The composition can, of course, comprise several cosmetic ingredients appearing in the above list.

Depending on their nature and the purpose of the composition, the normal cosmetic ingredients can be present in normal amounts which can be easily determined by those skilled in the art and which can be, for each ingredient, between 0.01% and 80% by weight. Those skilled in the art will take care to choose the ingredients included in the composition, and also the amounts thereof, such that they do not harm the properties of the compositions of the present invention.

The compositions used in the process according to the invention may be in any of the formulation forms conventionally used, and in particular in the form of an aqueous, alcoholic or aqueous-alcoholic, or oily solution or suspension; a solution or a dispersion of the lotion or serum type; an emulsion, in particular of liquid or semi-liquid consistency, of the O/W, W/O or multiple type; a suspension or emulsion of soft consistency of cream (O/W) or (W/O) type; an aqueous or anhydrous gel, or any other cosmetic form.

(pH)

The composition used in the process according to the present invention has a pH of from 8.0 to 12, preferably from 8.5 to 11.5, and more preferably from 9.0 to 11.0, which is measured at 25° C.

Thus, the composition used in the process according to the present invention is not anhydrous.

It is preferable that the pH of the composition used in the process according to the present invention be within ±2 relative to the pH which is equal to the pKa of the following equilibrium:

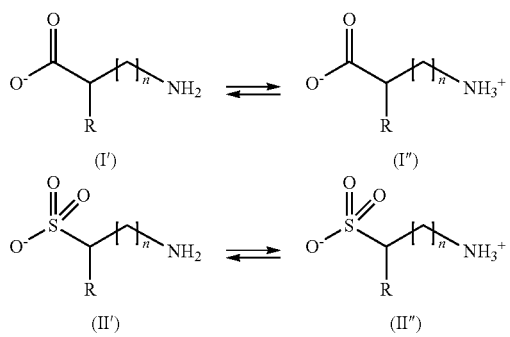

(Viscosity)

It is preferable that the composition used in the process according to the present invention have a viscosity of 800 mPa·s or more, more preferably 1,000 mPa·s or more, and even more preferably 1,500 mPa·s or more. The viscosity can be measured with a rotatory viscometer (Vismetron VS-A1: Rotor No. 3, 12 rpm, High, 30 seconds) at 25° C.

It is also preferable that the composition used in the process according to the present invention have a viscosity of 20,000 mPa·s or less, more preferably 15,000 mPa·s or less, and even more preferably 10,000 mPa·s or less.

It may be preferable that the composition used in the process according to the present invention have a viscosity of from 800 to 8,000 mPa·s, more preferably from 1,000 to 6,000 mPa·s, even more preferably from 1,500 to 4,000 mPa·s, and in particular from 2,000 to 3,000 mPa·s.

(Ammonia and Thiol Compound)

It is preferable that the composition used in the process according to the present invention be free of ammonia or a thiol compound. The term "free of ammonia or a thiol compound" means that the composition used in the process according to the present invention does not include a substantial amount of ammonia or a thiol compound. Preferably the composition used in the process according to the present invention includes 1% by weight or less, more preferably 0.5% by weight or less, and even more preferably 0.1% by weight or less of ammonia or a thiol compound, in particular no ammonia or the thiol compound.

Due to the very small amount or the absence of ammonia and/or thiol compound, malodor during the use of the composition used in the process according to the present invention is reduced or prevented.

The thiol compound here means a compound which has at least one thiol (—SH) group.

The thiol compound may be a reducing agent. The thiol reducing agent may be chosen from the group consisting of thioglycolic acid and derivatives thereof, in particular esters thereof such as glycerol or glycol monothioglycolate; thiolactic acid and derivatives thereof, in particular esters thereof such as glycerol monothiolactate; 3-mercaptopropionic acid and derivatives thereof, in particular esters thereof such as glycerol 3-mercaptopropionate and ethyleneglycol 3-mercaptopropionate; cysteamine and derivatives thereof, in particular $C_1$-$C_4$ acyl derivatives thereof such as N-acetylcysteamine and N-propionylcysteamine; mono-thioglycerol and derivatives thereof, in particular esters; cysteine and derivatives thereof, in particular esters such as N-acetylcysteine, N-alkanoylcysteine and cysteine alkyl esters; thioglycerine and derivatives thereof, in particular s-alkyl derivatives, and salts thereof.

As the above salts, mention may be made of, for example, ammonium salts; primary-, secondary- or tertiary-amine salts; alkaline metal salts; and, alkaline earth metal salts. As the primary-, secondary- or tertiary-amine, for example, monoethanolamine, di-isopropanolamine or triethanolamine, respectively, may be mentioned.

Other examples of the thiol reducing agent include, but are not limited to, sugar N-mercapto alkyl amides such as N-(mercapto-2-ethyl)gluconamide, β-mercaptopropionic acid and derivatives thereof; thiomalic acid; pantheteine; N-(mercaptoalkyl)ω-hydroxyalkyl amides such as those described in European Patent Application No. 0 354 835 and N-mono- or N,N-dialkylmercapto 4-butyramides such as those described in European Patent Application No. 0 368 763; aminomercaptoalkyl amides such as those described in European Patent Application No. 0 432 000 and alkylaminomercaptoalkylamides such as those described in European Patent Application No. 0 514 282; (2/3) hydroxy-2 propyl thioglycolate; and the hydroxy-2 methyl-1 ethyl thioglycolate-based mixture (67/33) described in French Patent Application No. 2 679 448.

(Reducing Agent and Oxidizing Agent)

The composition according to the present invention may comprise a reducing agent; however, it is preferable that the composition according to the present invention comprises a reduced amount of a reducing agent or an oxidizing agent, preferably free of a reducing agent or an oxidizing agent.

The term "free of a reducing agent or an oxidizing agent" means that the composition according to the present invention does not include a substantial amount of a reducing agent or an oxidizing agent. Preferably the composition according to the present invention includes 1% by weight or less, more preferably 0.5% by weight or less, and even more preferably 0.1% by weight or less of a reducing agent or an oxidizing agent, in particular no reducing agent or no oxidizing agent.

The reducing agent may be a thiol reducing agent or a non-thiol reducing agent. The thio reducing agent is as described above.

The non-thiol reducing agent here means a reducing agent with no thiol group. The non-thiol reducing agent may be chosen from the group consisting of sulfites, bisulfites, sulfinates, phosphines, sugars, reductones and hydrides. The non-thiol reducing agent may be selected from ammonium sulfites and bisulfites as well as metal sulfites and bisulfites, more preferably alkali metal or alkali earth metal sulfites and bisulfites, and more preferably sodium sulfites and bisulfites.

The oxidizing agent may be chosen from hydrogen peroxide, alkali metal bromates, ferricyanides peroxygenated salts, and compounds capable of producing hydrogen peroxide by hydrolysis. For example, the oxidizing agent can be chosen from aqueous hydrogen peroxide solution, urea peroxide, alkali metal bromates and persalts such as perborates and persulphates

[Process]

The composition according to the present invention may be intended for a process reshaping keratin fibers with heat.

The present invention relates to a reshaping process, in particular permanent waving, for keratin fibers, preferably the hair.

The reshaping process according to the present invention can be performed by:
applying onto the keratin fibers the composition described above;
heating the keratin fibers; and
optionally rinsing and/or drying the keratin fibers.

According to the process, the composition described above is applied to keratin fibers such as hair. The application of the composition may be performed by any means, such as a brush and a comb. It may be possible that the keratin fibers are left as they are for a certain amount of time, if necessary.

The composition which has just been described can be applied to dry or wet hair, preferably to dry hair.

The bath ratio of the applied composition may range from 0.1 to 10, more particularly from 0.2 to 5 and preferably between 0.5 and 3. The term "bath ratio" is intended to mean the ratio between the total weight of the applied composition and the total weight of keratin fibres to be treated.

Before or after the application of the composition described above to the keratin fibers, the keratin fibers may be subjected to mechanical tension for reshaping or deformation. The mechanical tension can be applied to the keratin fibers by any means to reshape or deform the keratin fibers to an intended shape. For example, the mechanical tension may be provided by at least one reshaping means selected from the group consisting of a curler, a roller, a clip, a plate and an iron. The reshaping means may comprise at least one heater. If the keratin fibers are rolled around a curler, this rolling-up may be performed on the entire length of the keratin fibers or, for example, on half the length of the keratin fibers. Depending on, for example, the desired hairstyle shape and amount of curls, the rolling-up may be performed with more or less thick locks.

Optionally, the keratin fibers may be placed in an occlusive or closed space. The occlusive space may be formed by at least one coating means. For example, a coating means is wound around keratin fibers to form the occlusive or closed space. A plurality of coating means may be used. The coating means may be rigid or flexible.

The coating means may comprise at least one member selected from the group consisting of a film and a sheet. The material of the film or the sheet is not limited. For example, the film or the sheet may comprise a thermoplastic or thermosetting resin, a paper, a textile, a bonnet, a metal foil such as aluminum foil, and the like. For example, the film or sheet may be set on a heating rod, a heating bar or a heating plate which is covered by keratin fibers.

The coating means may comprise the heat energy source. Therefore, for example, the film or sheet which includes a heater may be set on a rod, a bar, or a plate which is covered by keratin fibers.

The occlusive conditions can restrict the evaporation of evaporable components such as water in the above-described composition applied to keratin fibers, and therefore the temperature of the keratin fibers can be increased higher than that obtainable by a conventional heating process or device for the keratin fibers in open conditions. Furthermore, the keratin fibers can be heated effectively, and the keratin fibers can be heated evenly.

According to one variation of the present invention, the occlusive space may comprise apertures, the surface area of which is less than 5%, preferably less than 3% and more particularly less than 0.5% of the total surface area of the coating means. According to this variation, the total surface area of the coating means comprises the surface area of, when it is present, an opening means for the coating means.

The apertures may be passages, holes or orifices, which may allow an exchange of air between the occlusive space and the exterior thereof, especially when the reaction such as forming vapor inside the occlusive space is too great. On the other hand, a person skilled in the art could form the apertures such that the diffusion of heat in the occlusive space is not impaired.

The keratin fibers are then heated. The heating process can be performed by any heating means which can be freely controlled to realize the temperature desired for the process. The keratin fibers can be heated at 50° C. to 250° C., preferably 60° C. to 200° C., more preferably 70° C. to 150° C., and even more preferably 80° C. to 100° C., during the step of heating the keratin fibers. The heating process may be performed for an appropriate time which is required to treat the keratin fibers. The time length for the heating process is not limited, but it may be from 1 minute to 2 hours, preferably 5 minutes to 1 hour, and more preferably 10 minutes to 40 minutes After the heating, the keratin fibers are optionally rinsed, and preferably dried.

According to the process of the present invention, no or very little reducing or oxidizing agent will be used to reshape or deform keratin fibers such as hair. Therefore, as compared to conventional reshaping or deforming processes for keratin fibers which require reducing/oxidizing of the keratin fibers, the process of the present invention can reduce the time required for reshaping or deforming the keratin fibers.

Furthermore, the process of the present invention uses no or very little reducing or oxidizing agent, and therefore, the damage to the keratin fibers can be reduced as compared to the conventional processes which require the use of the reducing or oxidizing agent.

EXAMPLES

The present invention will be described in a more detailed manner by way of examples. However, these examples should not be construed as limiting the scope of the present invention.

Examples 1-4 and Comparative Examples 1-4

The following compositions according to Examples 1-4 and Comparative Examples 1-4, shown in Table 1, were prepared by mixing the ingredients shown in Table 1. The numerical values for the amounts of the ingredients shown in Table 1 are all based on "% by weight" as active raw materials.

TABLE 1

|  | Ex. 1 | Comp. Ex. 1 | Ex. 2 | Ex. 3 | Ex. 4 | Comp. Ex. 2 | Comp. Ex. 3 | Comp. Ex. 4 |
|---|---|---|---|---|---|---|---|---|
| Alanine | 10 | 5 | – | – | – | – | – | – |
| Glycine | – | – | 10 | – | – | – | – | – |
| Taurine | – | – | – | 10 | – | – | – | – |
| CHES | | | | | 10 | | | |
| Arginine | | | | | | 10 | | |
| Proline | – | – | – | – | – | – | 10 | – |
| Methionine | – | – | – | – | – | – | – | 10 |
| NaOH | qs pH 10.0 | qs pH 10.0 | qs pH 10.0 | qs pH 10.0 | qs pH 10.0 | – | qs pH 10.0 | qs pH 10.0 |
| HCl | – | – | – | – | – | qs pH 10.0 | – | – |
| Wave Intensity | ++ | + | ++ | ++ | ++ | ++ | – | + |
| Remaining Malodor | ++ | ++ | ++ | ++ | ++ | ++ | ++ | – |
| Conditioning | + | – | + | + | + | – | + | + |

CHES: 2-(Cyclohexylamino)ethanesulfonic acid

[Evaluation]

The compositions according to Examples 1-4 and Comparative Examples 1-4 were used for permanent waving of the hair.

1 g of a swatch of Chinese hair was wound around a perm roller with a diameter of 16 mm. Each of the compositions according to Examples 1-4 and Comparative Examples 1-4 in an amount of 2 g was applied to the hair. The perm roller was then covered with a wrapping, and plugged into a digital perm machine. After heating at 90° C. for 25 minutes, the wrapping was removed, and the hair was cooled down. The perm roller was then removed, and the hair was rinsed off with water and dried.

The panelists evaluated the wave intensity and usability provided by the compositions according to Examples 1-4 and Comparative Examples 1-4 in accordance with the criteria shown below.

(Wave Intensity)

Wave intensity: the greater the number of curls formed, the stronger the wave intensity is.

The criteria of the evaluation were as follows.
++: strong wave intensity
+: moderate wave intensity
–: poor wave intensity (Remaining Malodor)

Remaining Malodor: malodor remained after rinsing off was evaluated.

The criteria of the evaluation were as follows.
++: no malodor
+: almost no malodor
–: significant malodor (Conditioning)

Conditioning: conditioning feel was evaluated.
The criteria of the evaluation were as follows.
+: soft and smooth
–: stiff or tangle The results of the evaluations are shown in Table 1.

The composition according to Example 1 has a pH of 10.0, and includes a specific amino acid in an amount of more than 8% by weight relative to the total weight of the composition. The composition according to Example 1 provides good cosmetic properties, strong wave intensity and does not exhibit malodor.

The composition according to Comparative Example 1 has a pH of 10.0, and includes the same specific amino acid as Example 1, whereas the amount of the specific amino acid is less than 8% by weight relative to the total weight of the composition. The cosmetic properties provided by the composition according to Comparative Example 1 are inferior to those provided by Example 1and the wave intensity is also inferior.

The comparison of the evaluation results for Example 1 and Comparative Example 1 shows that the use of a composition which has a pH of from 8 to 12 and includes a specific amino acid which is within the scope of the (a) compound(s) used in the present invention in an amount of 8% by weight or more relative to the total weight of the composition is necessary to provide superior cosmetic effects and superior wave intensity.

The compositions according to Examples 2-4 have a pH of 10.0, and include another specific amino acid or an aminosulfonic acid which are within the scope of the (a) compound(s) used in the present invention in an amount of 8% by weight or more relative to the total weight of the composition. The compositions according to Examples 2-4 provide also good cosmetic properties, strong wave intensity and do not exhibit malodor.

Comparative Examples 2-4 have a pH of 10.0, and include another specific amino acid which is not within the scope of the (a) compound(s) used in the present invention in an amount of 8% by weight or more relative to the total weight of the composition. The cosmetic properties provided by the composition according to Comparative Example 2 are inferior to those provided by Examples 1-4 and the wave intensity provided by the compositions according to Comparative Examples 3 and 4 is inferior to those provided by Examples 1-4. In addition, the composition according to Comparative Example 4 exhibits significant malodor.

The comparison of the evaluation results for Examples 1-4 and Comparative Examples 2-4 show that the use of a composition which has a pH of from 8 to 12, and includes the (a) compound according to the present invention in an amount of 8% by weight or more relative to the total weight of the composition is necessary to provide superior cosmetic effects, a superior wave intensity without exhibiting malodor.

The invention claimed is:

1. A composition comprising:
   at least one compound (a) chosen from alkylaminosulfonic acids selected from 4-(2-hydroxyethyl)-1-piperazineethanesulfonic acid or 2-(cyclohexylamino)ethanesulfonic acid or compounds of the following formulae (I) or (II):

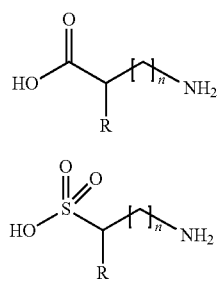

wherein:
   R is chosen from a hydrogen atom, or a linear or branched $C_1$-$C_5$ alkyl group; and
   n is 0 or 1; and
   at least one alkaline agent;
   wherein the at least one compound (a) is present in an amount of 8% to 15% by weight relative to the total weight of the composition;
   wherein the composition has a pH ranging from about 8 to about 12, and
   wherein the composition comprises less than 0.1% by weight of ammonia.

2. The composition according to claim 1, wherein the pH of the composition is within ±2 relative to the pH which is equal to the pKa of the following equilibrium:

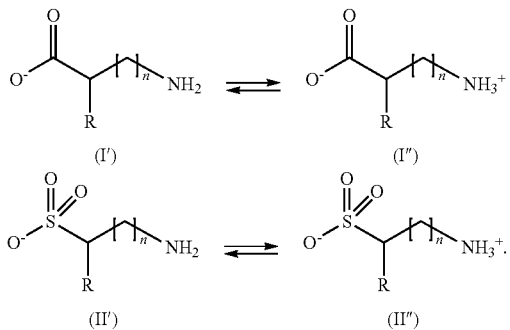

3. The composition according to claim 1, wherein the at least one compound (a) is chosen from glycine, alanine, β-alanine, isoleucine, leucine, 2-(cyclohexylamino)ethanesulfonic acid, and taurine.

4. The composition according to claim 1, wherein the at least one compound (a) is the only active ingredient for reshaping keratin fibers.

5. The composition according to claim 1, wherein the at least one alkaline agent is chosen from alkaline metal hydroxides, alkaline earth metal hydroxides, alkaline metal phosphates, monohydrogenophosphates, or mixtures thereof.

6. The composition according to claim 1, wherein the at least one alkaline agent is present in an amount ranging from about 0.1% to about 15% by weight, relative to the total weight of the composition.

7. The composition according to claim 1, wherein the composition does not comprise any ammonia or a thiol compound, or comprises less than 1% by weight of a thiol compound, relative to the total weight of the composition.

8. The composition according to claim 1, wherein the composition does not comprise any reducing agent or oxidizing agent, or comprises less than 1% by weight of a reducing agent or an oxidizing agent, relative to the total weight of the composition.

9. A process for reshaping keratin fibers, comprising:
   applying to the keratin fibers a composition comprising at least one compound (a) chosen from alkylaminosulfonic acids selected from 4-(2-hydroxyethyl)-1-piperazineethanesulfonic acid or 2-(cyclohexylamino)ethanesulfonic acid or compounds of the following formulae (I) or (II):

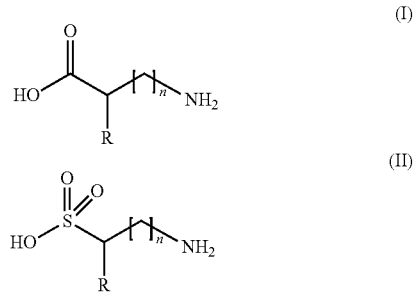

wherein:
   R is chosen from a hydrogen atom, or a linear or branched $C_1$-$C_5$ alkyl group; and
   n is 0 or 1, and
   at least one alkaline agent;
   wherein the at least one compound (a) is present in an amount of 8% to 15% by weight, relative to the total weight of the composition,
   the composition has a pH ranging from about 8 to about 12, and
   wherein the composition comprises less than 0.1% by weight of ammonia;
   heating the keratin fibers; and
   optionally rinsing and/or drying the keratin fibers.

10. The process according to claim 9, wherein the keratin fibers are heated to a temperature of at least about 80° C.